United States Patent [19]

Cerwin et al.

[11] 4,317,451
[45] Mar. 2, 1982

[54] PLASTIC SURGICAL STAPLE

[75] Inventors: Robert J. Cerwin, Pittstown; William P. McVay, Somerville, both of N.J.

[73] Assignee: Ethicon, Inc., Somerville, N.J.

[21] Appl. No.: 122,557

[22] Filed: Feb. 19, 1980

[51] Int. Cl.³ ............... A61B 17/12; A61B 17/08; F16B 15/00; B31B 1/00
[52] U.S. Cl. ............... 128/325; 128/335; 128/337; 227/19; 227/DIG. 1; 411/457
[58] Field of Search ........... 128/325, 326, 330, 334 R, 128/335, 336, 337; 227/19, 119, DIG. 1; 411/457, 471, 472, 473, 475; 29/243.56, 816

[56] References Cited

U.S. PATENT DOCUMENTS

| | | | |
|---|---|---|---|
| 1,728,316 | 9/1929 | Von Wachenfeldt | 128/334 R |
| 2,881,762 | 4/1959 | Lowrie | 128/337 |
| 2,887,110 | 5/1959 | Roeschmann | 128/334 R |
| 3,068,870 | 12/1962 | Levin | 227/DIG. 1 |
| 3,604,425 | 9/1971 | LeRoy | 227/DIG. 1 |
| 3,620,218 | 11/1971 | Schmitt et al. | 128/334 R |
| 3,643,851 | 2/1972 | Green et al. | 128/334 R |
| 3,646,801 | 3/1972 | Caroli | 128/334 R |
| 3,739,773 | 6/1973 | Schmitt et al. | 128/92 BC |
| 3,873,016 | 3/1975 | Fishbein | 227/83 |
| 3,875,648 | 4/1975 | Bone | 227/19 |
| 4,014,492 | 3/1977 | Rothfuss | 227/19 |
| 4,021,890 | 5/1977 | Kurosaki | 411/472 |
| 4,060,089 | 11/1977 | Noiles | 128/325 |
| 4,109,844 | 8/1978 | Becht | 227/120 |
| 4,162,678 | 7/1979 | Fedotov et al. | 128/334 R |

FOREIGN PATENT DOCUMENTS 790997  11/1935  France ................. 128/337

Primary Examiner—Robert W. Michell
Assistant Examiner—C. W. Shedd
Attorney, Agent, or Firm—Robert L. Minier

[57] ABSTRACT

A one-piece, self-locking, molded plastic staple useful as a tissue fixation device in surgical procedures. The staple has opposed, pointed, L-shaped legs secured to a horizontal bridging member. Each leg has an extension which is engaged by a locking bar extending between the extensions when the staple is closed by forcing the legs through a 90° arc. The staples may be extruded or molded of absorbable or nonabsorbable polymeric materials.

26 Claims, 12 Drawing Figures

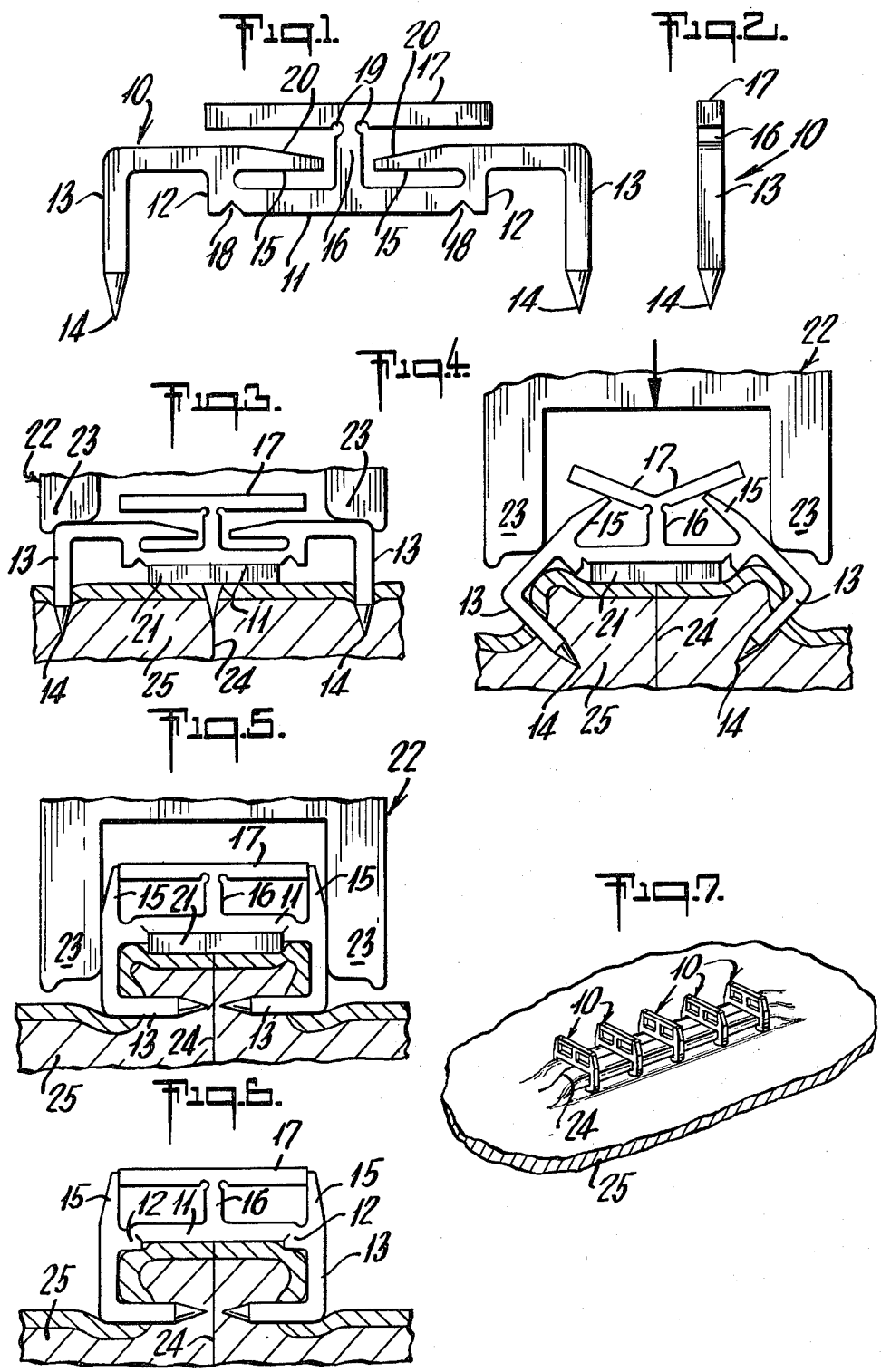

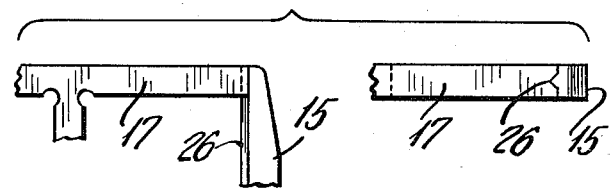
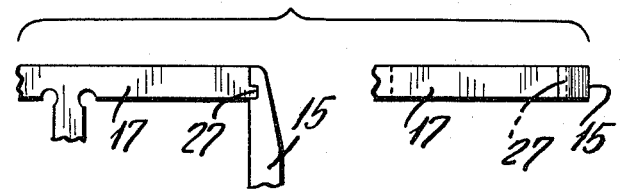
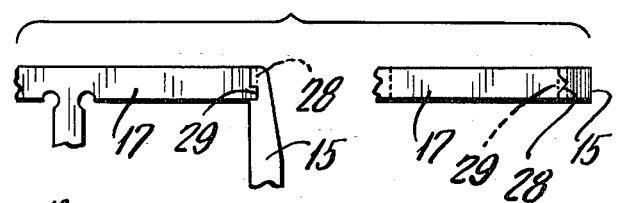
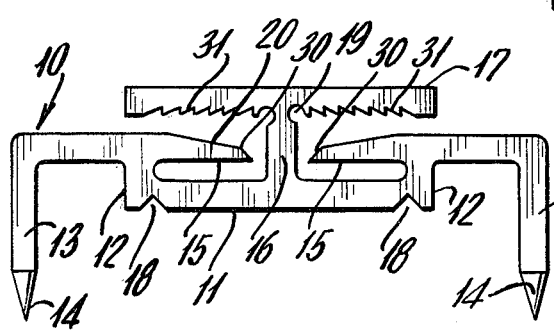
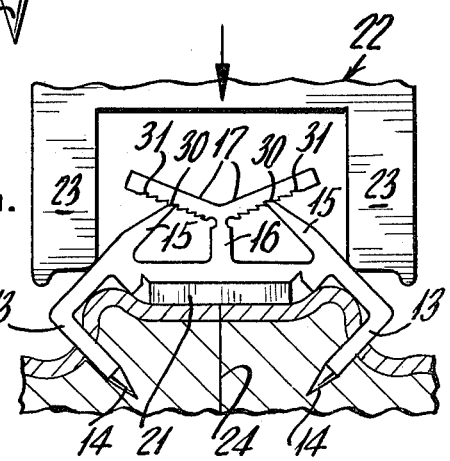

PLASTIC SURGICAL STAPLE

BACKGROUND

In recent years, surgical staples have come into wide use as an alternative to sutures in closing incisions of skin, fascia, and internal organs. Staples have an advantage over sutures in some applications due to the speed and ease with which staples may be placed. In addition, special stapling instruments have been designed which place an entire row or ring of staples in a single operation to further simplify and speed up the surgical procedure.

Surgical staples currently in use are fabricated of tantalum or stainless steel wire having sufficient tensile strength and bending modulus to assure that the staple will remain closed after it has been set in place. Although it has long been recognized that staples made of plastic or polymeric materials would be desirable for use in surgical applications, the development of such staples has been difficult due to inherent resiliency of such materials. Staples of known plastic compositions and of the same configuration as a metallic staple do not have sufficient strength and bending modulus to stay closed after being set in place. One approach to utilizing plastic materials in surgical stapling procedures has been to provide cooperating mechanical means to secure the staple in its set configuration. U.S. Pat. No. 2,881,762 proposed a circular, open ring-type staple wherein the ends were designed to pierce the tissue, overlap and lock to form a closed ring through the tissue similar to a knotted suture. More recently, a two-piece staple was suggested in U.S. Pat. No. 4,060,089 wherein a pronged fastener strip pierced the tissue and a cooperating retainer strip gripped the prongs on the opposite side of the tissue. This device is limited in its application to situations where access to both sides of the tissue is available, and a special tool is required to apply the device.

It is an object of the present invention to provide a plastic staple which functions in a manner analagous to that of a metallic staple, i.e., a one-piece device which is applied from one side of the tissue. It is a further object of the present invention to provide a plastic staple which can be set with a tool of conventional design. It is yet a further object of the present invention to provide plastic staples fabricated of biologically absorbable polymers as well as of conventional nonabsorbable polymers. These and other objects of the present invention will be apparent from the ensuing description and claims.

SUMMARY

A one-piece, self-locking molded plastic staple is provided which, in its open configuration, comprises, in a vertical plane, two outward and downward pointed staple legs secured to a central bridging member by short, vertical leg support members. Each staple leg has an extension extending inward from the leg support member toward the center of and above the bridging member. A horizontal staple leg locking bar is mounted to the central bridging member by a vertical support post extending between the staple leg extensions. The locking bar is parallel to and coextensive with the central bridging member.

The staple is enplaced in the tissue with a conventional stapling mechanism comprising an anvil and forming die. The anvil supports the central bridging member while the forming die acts upon each leg member, causing the legs and leg support members to pivot 90°. As the staple closes, the legs pierce the tissue and form a box-like configuration enclosing a segment of tissue with the points of the staple leg approaching one another within the tissue. As the staple is being closed, the leg extension members deflect the locking bar until the ends of the bar are bypassed, whereupon the bar snaps in place between the leg extensions locking the staple in the closed position.

The staple may be machined or molded of any suitable polymeric material including both biologically absorbable and nonabsorbable compositions. Preferred absorbable materials include polymers of lactide and glycolide. Preferred nonabsorbable materials include nylon and polypropylene.

DESCRIPTION OF DRAWINGS

FIG. 1 is an elevational view of a surgical staple according to the present invention.

FIG. 2 is an end elevational view of the staple of FIG. 1.

FIG. 3 is a view showing the staple of FIG. 1 in its relation to the forming anvil, the forming die and the wound which is to be closed.

FIG. 4 is a view similar to FIG. 3 showing the staple in the process of being formed.

FIG. 5 is a similar view showing the staple completely formed and closing the wound.

FIG. 6 is a view similar to FIG. 5 showing the wound after the forming tool has been removed.

FIG. 7 is a perspective view of a wound properly closed by a plurality of staples according to the invention.

FIG. 8 is a side and top view of a portion of the closed staple illustrating a locking engagement for the staple leg.

FIG. 9 is a view similar to FIG. 8 illustrating another locking engagement.

FIG. 10 is a similar view illustrating a further locking engagement.

FIG. 11 is an elevational view of another embodiment of a surgical staple according to the present invention.

FIG. 12 is a view of the staple of FIG. 11 in a partially closed configuration.

DESCRIPTION

With reference to FIGS. 1 and 2, there is illustrated staple 10 of the present invention having horizontal bridging member 11 spanning the width of the staple and terminating at each end in an upward extending staple leg support member 12. L-shaped staple leg 13 extends horizontally outward and downward from each leg support member and terminates in tissue piercing point 14. Horizontal staple leg extensions 15 extend inwardly from each leg support member toward the center of the staple, terminating with a central space between the ends thereof.

Center post 16 extends upward between the staple leg extensions from the horizontal bridging member, and horizontal staple leg locking bar 17 is secured to the upper end of the center post in a spaced relationship to staple leg extensions 15.

Additional features included in the preferred embodiment of the staple illustrated in FIG. 1 include V-notches 18 and relief grooves 19 which facilitate the operation of the staple as hereinafter explained. Also as illustrated in FIG. 1, staple leg extensions 15 are tapered at 20 on the upper surface thereof for reasons explained below.

The emplacement of staple 10 to approximate the tissue of a skin wound is illustrated progressively in FIGS. 3 through 6. The staple is closed by use of a conventional staple-forming tool which includes anvil 21 and a bridging die 22 as illustrated in part in FIGS. 3-5.

Referring now to FIG. 3, staple 10 is positioned in the forming tool by suitable means with bridging member 11 supported by anvil 21 and the extremities 23 of die 22 abutting staple legs 13. The forming tool and staple are placed directly over wound 24 in tissue 25. Since the staple legs extend below the level of the anvil, the legs are caused to make initial contact with the tissue as the forming tool is positioned over the wound.

The staple is closed and the wound secured by lowering die 22 beyond anvil 21 as illustrated in FIGS. 4 and 5. In FIG. 4, as the staple begins to close, legs 13 penetrate into the skin in a tissue gathering arc as staple leg support members 12 pivot about the ends of bridging member 11. V-notches 18 form hinge points to facilitate this pivoting action. Simultaneously, staple leg extensions 15 rotate upward against locking bar 17 which is deflected to permit passage of the extensions. Relief grooves 19 form hinge points which relieve stress during the deflection of the locking bar. Taper 20 on the upper surface of the staple leg extensions also permits easier passage of the extensions past the locking bar.

As die 22 is fully depressed as illustrated in FIG. 5, staple leg members 13 pivot a full 90° within the tissue. Staple leg extensions 15 by-pass the ends of locking bar 17, and the resiliency of the plastic material causes the locking bar to return to its initial horizontal position, now between leg extensions 15, effectively locking the staple in its formed or closed position. Once the staple is so locked, die 22 is raised and the forming tool removed leaving the staple securely fastened in the tissue across the wound with the edges of the wound properly everted as illustrated in FIG. 6. FIG. 7 illustrates a complete incision properly closed with a series of staples in accordance with the present invention.

The staples of the present invention are preferably rectangular in cross section except for the staple legs which may be made cylindrical and/or tapered if desired for ease of tissue penetration. The staple leg extensions 15 and the ends of locking bar 17 are either flat or provided with recessed surfaces in the locked position to prevent the subsequent disengagement of these surfaces once the staple has been formed.

FIGS. 8-10 illustrate various mating arrangements which may be employed between the staple leg extensions and the ends of the locking bar. In FIG. 8, the inside of leg extension 15 is provided with a raised rib 26 while the end of bar 17 is provided with a corresponding recessed groove. This arrangement restricts lateral displacement of the staple leg extension once the staple has been formed into its locked position.

FIG. 9 illustrates a tongue and groove interlock at 27 between the end of locking bar 17 and the inside of leg extension 15. This arrangement restricts the vertical displacement of locking bar 17 once the staple has been closed.

FIG. 10 illustrates one arrangement for restricting both lateral and vertical movement of the leg extension and locking bar once the staple has been closed. In this embodiment, leg extension 15 is provided with a short raised rib 28 at the very tip thereof having a length of about one-half the thickness of locking bar 17. The end of the locking bar is provided with a corresponding groove to receive rib 28 as illustrated. A horizontal tongue and groove interlock immediately below rib 28 completes the arrangement.

FIGS. 11 and 12 illustrate a variation of the staple of FIG. 1, wherein locking bar 17 is provided with a series of ratchet teeth 31 on the lower surface thereof, and leg extensions 15 have angled tips 30 adapted to engage said ratchet teeth as the staple is closed. Such a clip has an advantage over the clip of FIG. 1 in special situations where less than full closure of the clip may be desired. The clip of FIG. 11 may accordingly be closed to the degree as illustrated, for example, in FIG. 12, and the applier removed to leave the clip in the partially closed configuration. The clip of FIG. 11 may also be fully closed if desired.

While the staple of the present invention has been described and illustrated in a skin closure application, the staple may be used for closing fascia or internal organs as well. Since the staple is adapted for use with staple emplacement tools of a conventional design, the use of the staple in cartridge fed, repeating stapling instruments or in instruments which set a plurality of staples in a straight line or in a circle with a single firing is also included within the scope of this invention. It is understood that some modification of existing stapling instruments may be required to physically accommodate the staples of the present invention, but such modification is well within the present skill of the instrument manufacturers.

The staples of the present invention may be constructed in sizes corresponding to the size of conventional metallic staples. In an average size staple, the horizontal bridging member may be from about 0.25 to 0.6 cm, while the L-shaped staple leg members are sized proportionately as illustrated for example, in FIG. 1.

The staples may be fabricated by any suitable plastic forming technique including extrusion and injection molding depending upon staple design and material of fabrication which may be any of several polymeric compositions known to be biocompatible in surgical applications. Nylon, polypropylene, polyester and polysulfone are illustrative of materials which may be used to form nonabsorbable staples. Homopolymers and copolymers of lactide, glycolide and p-dioxanone are illustrative of materials which may be used to fabricate absorbable staples for internal application. Other suitable polymeric compositions are known to those familiar with the art and may also be used in accordance with the present invention.

Nonabsorbable staples of, for example, polypropylene or nylon may be used in internal applications where absorption is not an important factor. Where such staples are used externally, they are easily removed after the wound has sufficiently healed by merely clipping center post 16 to remove locking bar 17 from the staple. The staple legs may thereupon be rotated back to their original position as illustrated in FIG. 1 and removed from the tissue with minimal discomfort to the patient.

The following claims are drawn with respect to the preceding description and associated figures, and references to orientation are for purposes of understanding and not of limitation. The clips may be oriented in any manner desired prior to or during use.

What is claimed is:

1. A one-piece, self-locking, plastic surgical staple comprising, in a vertical plane,
    a horizontal bridging member spanning the width of the staple and terminating at each end in an upward extending staple leg support member,
    an L-shaped staple leg extending horizontally outward and downward from each leg support member and terminating in a tissue-piercing point,
    a staple leg extension extending inwardly from each staple leg at the leg support member and terminating with a space between opposing ends of said extensions,
    a center post extending vertically upward from said bridging member and through said space between the opposing ends of said extensions, and
    a horizontal staple leg locking bar secured to said center post and extending horizontally in a closely spaced relationship adjacent said staple leg extensions and staple leg support members,
    said staple leg support members and staple legs secured thereto being pivotable with respect to said horizontal bridging member to close said staple legs, whereupon said staple leg extensions deflect said locking bar and are thereafter engaged by said locking bar to maintain said staple legs in their closed position.

2. The staple of claim 1 wherein an integral hinge is provided at the juncture of each staple leg support member and said horizontal bridging member.

3. The staple of claim 1 wherein a relief groove is provided at each juncture of the locking bar and the center post.

4. A staple of claim 1 wherein the length of said locking bar is coextensive with the width of said horizontal bridging member and the length of said leg support members.

5. The staple of claim 1 wherein each staple leg extension is tapered away from the locking bar.

6. The staple of claim 1 having members of a generally rectangular cross section.

7. The staple of claim 1 wherein the staple leg members have a circular cross section.

8. The staple of claim 1 wherein said staple leg members are adapted to pivot 90° with respect to said horizontal bridging member, and said staple leg extensions bypass said locking bar and are thereafter engaged by the ends of said locking bar to maintain said staple legs in their closed position.

9. The staple of claim 8 wherein said leg extensions and the ends of said locking bar are provided with interlocking means which are engaged when the staple is closed.

10. The staple of claim 9 wherein said interlocking means comprise V-shaped surfaces adapted to nest when said staple is closed.

11. The staple of claim 9 wherein said interlocking means comprise a tongue and groove adapted to engage when said staple is closed.

12. The staple of claim 1 wherein said staple leg locking bar includes a series of ratchet teeth on the lower surface thereof, and said staple leg extensions include angled tips adapted to engage said ratchet teeth as said clip is closed.

13. The staple of claim 1 comprising an absorbable polymeric composition.

14. The staple of claim 13 wherein said absorbable polymeric composition is a homopolymer or copolymer of lactide, glycolide, or p-dioxanone.

15. The staple of claim 1 comprising a nonabsorbable polymeric composition.

16. The staple of claim 15 wherein said nonabsorbable polymeric composition is selected from the group consisting of nylon, polyester, polypropylene, and polysulfone.

17. In combination with a stapling tool having a forming anvil and a cooperating forming die, a one-piece self-locking plastic surgical staple comprising, in a vertical plane and prior to closure,
    a horizontal bridging member spanning the width of the staple and terminating at each end in an upward extending staple leg support member,
    an L-shaped staple leg extending horizontally outward and downward from each leg support member and terminating in a tissue-piercing point,
    a staple leg extension extending inwardly from each staple leg and leg support member and terminating with a space between opposing ends of said extensions,
    a center post extending vertically upward from said bridging member and through said space between the opposing ends of said extensions, and
    a horizontal staple leg locking bar secured to said center post and extending horizontally in a closely spaced relationship adjacent said staple leg extensions and staple leg support members,
    said forming anvil having a width substantially equal to the width of said horizontal bridging member,
    said forming die having two downward projecting extremities spaced to engage the staple legs when the staple is centered on the anvil, the distance between said extremities corresponding substantially to the width of the staple after closure,
    said anvil and said forming die being operable to close said staple by pivoting said staple leg support members and staple legs with respect to said horizontal bridging member, whereupon said staple leg extensions deflect said locking bar and are thereafter engaged by said locking bar to maintain said staple legs in their closed position.

18. The combination of claim 17 wherein said staple leg support members are adapted to pivot 90° with respect to said horizontal bridging members, to deflect and bypass the ends of said bridging member, said staple, when closed, having a dual box-like configuration formed by the staple legs on one side of the horizontal bridging member and the staple leg extensions and locking bar on the other side of the horizontal bridging member.

19. The combination of claim 18 wherein the staple leg extensions and locking bar include interlocking means which are engaged when said staple is closed to form said box-like configuration.

20. The combination of claim 17 wherein the tissue-piercing points of the staple legs extend beyond the plane of the anvil when the staple is centered on the anvil prior to closure.

21. A one-piece, self-locking, surgical staple comprising:
    a bridging member spanning the width of the staple;
    a staple leg joined to each end of said bridging member by hinge means and terminating in a tissue-piercing segment; and
    locking means comprising a T-shaped locking bar having a stem extending from the center of the bridging member and a deflectable cross member, said locking means cooperatively engaging to prevent the reverse rotation of said legs when the staple legs are closed and locked in position upon rotation about said hinge means.

22. The staple of claim 21 wherein the staple legs are L-shaped and the tissue piercing segment is oriented at right angles to the primary axis of the bridging member.

23. The staple of claim 21 wherein the rigid staple leg extension extending from each staple leg lies between said bridging member and said cross member of said locking means when the staple is in the open position.

24. The staple of claim 23 wherein the cross member of the locking bar is deflected by said staple leg extensions as the staple legs are rotated about 90 degrees, and said staple leg extensions are thereafter engaged by the ends of said locking bar.

25. The staple of claim 23 wherein the surface of the cross member of said locking bar confronting said staple leg extension includes ratchet teeth and the ends of said staple leg extensions provide a cooperative pawl, whereby said staple leg extensions are engaged stepwise by said locking bar as said staple legs are rotated about said hinge means.

26. The staple of claim 23 wherein said T-shaped locking bar includes stress relief grooves at the juncture of the cross member and stem member.

* * * * *